United States Patent [19]

Harandi et al.

[11] Patent Number: 4,935,568
[45] Date of Patent: Jun. 19, 1990

[54] MULTISTAGE PROCESS FOR OXYGENATE CONVERSION TO HYDROCARBONS

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 279,616

[22] Filed: Dec. 5, 1988

[51] Int. Cl.⁵ .............................................. C07C 2/02
[52] U.S. Cl. ..................................... 585/300; 585/301; 585/302; 585/315; 585/316; 585/329; 585/533; 585/640
[58] Field of Search ............... 585/300, 301, 302, 315, 585/316, 329, 533, 640

[56] References Cited
U.S. PATENT DOCUMENTS

| | | | |
|---|---|---|---|
| 4,497,968 | 2/1985 | Wright et al. | 585/533 |
| 4,665,268 | 5/1987 | Lee et al. | 585/640 |
| 4,740,645 | 4/1988 | Garwood et al. | 585/533 |
| 4,751,341 | 6/1988 | Rodewald | 585/533 |
| 4,788,366 | 11/1988 | Harandi et al. | 585/301 |

Primary Examiner—Curtis R. Davis
Attorney, Agent, or Firm—Alexander J. McKillop; Charles J. Speciale; L. G. Wise

[57] ABSTRACT

A continuous multistage process for preparing gasoline and/or distillate range hydrocarbons from lower molecular weight oxygenate feedstock wherein hydrocarbon yield is increased by recovering a vapor stream rich in ethene from an oxygenates conversion stage and reacting the ethene in a high severity reaction zone containing high activity zeolite catalyst.

48 Claims, 2 Drawing Sheets

MULTISTAGE PROCESS FOR OXYGENATE CONVERSION TO HYDROCARBONS

FIELD OF THE INVENTION

This invention relates to a multi-stage process for converting organic oxygenate material, such as methanol or dimethylether (DME) to liquid hydrocarbons. In particular it provides a continuous process for producing gasoline and/or distillate range hydrocarbons by oligomerizing olefins obtained from a methanol-to-olefins ("MTO") type process.

BACKGROUND OF THE INVENTION

Recent developments in zeolite catalysts and hydrocarbon conversion processes have created interest in utilizing olefinic feedstocks for producing $C_5+$ gasoline, diesel fuel, etc. In addition to the basic work derived from ZSM-5 type zeolite catalysts, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_2-C_5$ alkenes. U.S. Pat. Nos. 3,960,978 and 4,021,502 (Plank, Rosinski and Givens) disclose conversion of $C_2-C_5$ olefins, alone or in admixture with paraffinic components, into higher hydrocarbons over crystalline zeolites having controlled acidity. Garwood et al have also contributed improved processing techniques to the MOGD system, as in U.S. Pat. Nos. 4,150,062 4,211,640, and 4,227,992. The above-identified disclosures are incorporated herein by reference.

Conversion of lower olefins, especially propene and butenes, over HZSM-5 is effective at moderately elevated temperatures and pressures. The conversion products are sought as liquid fuels, especially the $C_5+$ aliphatic and aromatic hydrocarbons. Olefinic gasoline can be produced in good yield by the MOGD process and may be recovered as a product or recycled to the reactor system for further conversion to distillate-range products. Operating details for typical MOGD units are disclosed in copending U.S. patent applications Ser. No. 488,834, filed Apr. 26, 198 (Owen et al), now U.S. Pat. No. 4,456,779 and Ser. No. 481,704, filed Apr. 4, 1983 (Tabak), incorporated herein by reference.

In addition to their use as shape selective oligomerization catalysts, the medium pore ZSM-5 type catalysts are useful for converting methanol and other lower aliphatic alcohols and/or corresponding ethers to olefins. Particular interest has been directed to a catalytic process for converting low cost methanol to valuable hydrocarbons rich in ethene and lower alkenes. Various processes are described in U.S. Pat. No. 3,894,107 (Butter et al), U.S. Pat. No. 3,928,483 (Chang et al), U.S. Pat. No. 4,025,571 (Lago), U.S. Pat. No. 4,506,106 (Hsia et al), and U.S. Pat. No. 4,579,999 (Gould et al). Significance of the methanol-to-olefins ("MTO") type processes, especially for producing ethene, is discussed in Hydrocarbon Processing, Nov. 1982, pp. 117–120.

SUMMARY OF THE INVENTION

The present invention is a continuous multi-stage process for increasing the yield of liquid hydrocarbons boiling in the gasoline and distillate range from a feedstock comprising $C_1-C_4$ aliphatic oxygenates. The process comprises contacting the feedstock in a primary fluidized bed reaction zone with a shape selective medium pore crystalline metallosilicate catalyst under oxygenate conversion conditions to obtain a primary effluent comprising ethylene and $C_3+$ olefins; withdrawing the primary effluent; separating the primary effluent into a gaseous stream rich in ethylene and a liquid stream comprising $C_3+$ olefins; contacting the liquid stream comprising $C_3+$ olefins with a shape selective medium pore crystalline metallosilicate catalyst in a fixed bed reaction zone at elevated temperature and pressure to obtain a product stream comprising hydrocarbons boiling in the gasoline and distillate range; contacting the ethylene-rich stream with a shape selective medium pore crystalline metallosilicate catalyst in a secondary fluidized bed reaction zone under oligomerization conditions to obtain a secondary effluent comprising unreacted ethylene and heavier hydrocarbons; withdrawing the secondary effluent; separating the secondary effluent into a gaseous stream comprising ethylene and a liquid stream comprising heavier hydrocarbons; and adding at least a portion of the liquid stream comprising heavier hydrocarbons to the fixed bed reaction zone. A product comprising hydrocarbons boiling in the gasoline and/or distillate range is withdrawn from the fixed bed reaction zone.

Other objects and features of the invention will be seen in the following description and drawings.

DETAILED DESCRIPTION OF THE INVENTION

In this description, metric units and parts by weight are employed unless otherwise stated.

Catalyst versatility permits similar zeolites to be used in the fluidized bed oxygenate conversion reactor, the fluidized bed olefins oligomerization reactor, and the fixed bed MOGD reactor. The catalysts preferred for use herein include the medium pore shape selective crystalline aluminosilicate zeolites having a silica to alumina ratio of at least 12, a constraint index of about 1 to 12 and fresh acid cracking activity of about 10–250.

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The oligomerization catalysts preferred for use herein include the medium pore (i.e., about 5–7Å) shape-selective crystalline aluminosilicate zeolites having a silica-to-alumina ratio of at least 12, a constraint index of about 1 to 12 and fresh acid cracking alpha-value of about 10-250. Representative of the ZSM-5 type zeolites are ZSM-5, ZSM-11, ZSM-12, ZSM-22, ZSM-23, ZSM-35 and ZSM-38. ZSM-5 is disclosed in U.S. Pat. No. 3,702,886 and U.S. Pat. No. Re. 29,948 (Argauer et al). Other suitable zeolites are disclosed in U.S. Pat. Nos. 3,709,979 (Chu); U.S. Pat. No. 4,076,979 (Walter et al), U.S. Pat. No. 3,832,449 (Rosinski et al); U.S. Pat. No. 4,076,842 (Plank et al); U.S. Pat. No. 4,016,245 (Plank et al); U.S. Pat. No. 4,414,423 (Miller); U.S. Pat. No. 4,417,086 (Miller); U.S. Pat. No. 4,517,396 (Hoek et al) and U.S. Pat. No. 4,542,251 (Miller). The disclosures of these patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified. A typical zeolite catalyst component having Bronsted acid sites may consist essentially of aluminosilicate ZSM-5 zeolite with 5 to 95 wt. % silica and/or alumina binder These siliceous zeolites may be employed in their acid forms, ion exchanged or impregnated with one or more suitable metals, such as Ga, Pd, Zn, Ni, Co and/or other metals of Periodic Groups III to VIII. The zeolite may include a hydrogenation-dehydrogenation component (sometimes referred to as a hydrogenation component) which is generally one or more metals of group IB, IIB, IIIB, VA, VIA or VIIIA of the Periodic Table (IUPAC), especially aromatization metals, such as Ga, Pd, etc. Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (e.g., ionic $Ni^{+2}$, and a shape-selective medium pore acidic oligomerization catalyst, such as ZSM-5 zeolite) which components may be present in admixture or combined in a unitary bifunctional solid particle.

Certain of the ZSM-5 type medium pore shape selective catalysts are sometimes known as pentasils. In addition to the preferred aluminosilicates, the borosilicate, ferrosilicate and "silicalite" materials may be employed.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02-1 micron being preferred. In order to obtain the desired particle size for fluidization, the zeolite catalyst crystals are bound with a suitable inorganic oxide, such as silica, alumina, etc. to provide a zeolite concentration of about 5 to 95 wt. %. In the description of preferred embodiments a 25% H-ZSM-5 catalyst contained within a silica-alumina matrix and having a fresh alpha value of about 80 is preferred.

The conversion of aliphatic oxygenates such as methanol and dimethylether to olefins is a process well-known in the art. This methanol-to-olefins ("MTO") type process can be optimized to produce a major fraction of $C_2-C_4$ olefins. The $C_3+$ olefins are a valuable feed to the industrial process known as Mobil Olefins to Gasoline/Distillate ("MOGD"). Ethene is not as easily converted to more valuable hydrocarbons, and therefore it is advantageous to separate ethene from an olefinic feedstock for the MOGD process.

It is a purpose of the present invention to upgrade ethene-rich streams to more easily processed $C_3+$ olefinic materials.

In its simplest form, the present process comprises contacting a $C_1-C_4$ aliphatic oxygenate feedstock under oxygenate conversion conditions in a primary fluidized bed reaction system with a crystalline medium pore shape selective zeolite catalyst; withdrawing a product effluent comprising ethene and $C_3+$ olefins; separating the product effluent into a primary bottoms stream comprising $C_3+$ olefins and a primary overhead stream comprising ethene; and contacting the primary overhead stream comprising ethene under high severity oligomerization conditions in a secondary fluidized bed reaction system with a crystalline medium pore shape selective zeolite catalyst.

The process further comprises withdrawing from the secondary fluidized bed reaction system a product comprising unreacted ethene and $C_3+$ olefins; and adding at least a portion of withdrawn product to the primary fluidized bed reaction system.

In the secondary fluidized bed reaction severity conditions can be controlled to optimize yield of $C_4-C_9$ aliphatic hydrocarbons. It is understood that aromatics and light paraffin production is promoted by those zeolite catalysts having a high concentration of Bronsted acid reaction sites. Accordingly, an important criterion is selecting and maintaining catalyst inventory to provide either fresh catalyst having acid activity or by controlling catalyst deactivation and regeneration rates to provide an apparent average steady state alpha value of about 2 to 20.

Reaction temperatures and contact time are also significant factors in the reaction severity, and the process parameters are followed to give a substantially steady state condition wherein the reaction severity index (R.I.) is maintained to yield a desired weight ratio of propane to propene. It is preferred to operate the steady state fluidized bed unit to hold the R.I. at about 0.1:1 to 1:1. While reaction severity is advantageously expressed as the weight ratio of propane:propene in the gaseous phase, it may also be approximated by the analogous ratios of butanes:butenes, pentanes:pentenes, or the average of total reactor effluent alkanes:alkenes in the $C_3-C_5$ range. The optimum value will depend upon the exact catalyst composition, feedstock and reaction conditions.

Particle size distribution can be a significant factor in achieving overall homogeneity in turbulent regime fluidization. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt % of the total catalyst in the reaction zone in the size range less than 32 microns. This class of fluidizable particles is classified as Geldart Group A. Accordingly, the fluidization regime is controlled to assure operation between the transition velocity and transport velocity. Fluidization conditions are substantially different from those found in non-turbulent dense beds or transport beds. Turbulent regime fluidization conditions for the conversion of ethylene are disclosed in U.S. Pat. No. 4,746,762 (Avidan et al), incorporated herein by reference.

Several useful parameters contribute to fluidization in the turbulent regime in accordance with the process of the present invention. When employing a ZSM-5 type zeolite catalyst in fine powder form such a catalyst should comprise the zeolite suitably bound or impregnated on a suitable support with a solid density (weight of a representative individual particle divided by its apparaent "outside" volume) in the range from 0.6-2 g/cc, preferably 0.9-1.6 g/cc. The catalyst particles can be in a wide range of particle sizes up to about 250 microns, with an average particle size between about 20 and 100 microns, preferably in the range of 10-150 microns and with the average particle size between 40 and 80 microns. When these solid particles are placed in a fluidized bed where the superficial fluid velocity is 0.3-2 m/s, operation in the turbulent regime is obtained. Those skilled in the art will appreciate that at higher pressures, a lower gas velocity may be employed to ensure operation in the turbulent fluidization regime.

Under optimized process conditions the turbulent bed has a superficial vapor velocity of about 0.3 to 2 meters per second (m/sec). At higher velocities entrainment of fine particles may become excessive and beyond about 3 m/sec the entire bed may be transported out of the reaction zone. At lower velocities, the formation of large bubbles or gas voids can be detrimental to conversion. Even fine particles cannot be maintained effectively in a turbulent bed below about 0.1 m/sec.

A convenient measure of turbulent fluidization is the bed density A typical turbulent bed has an operating density of about 100 to 500 kg/m3, preferably about 300 to 500 kg/m$^3$, measured at the bottom of the reaction zone, becoming less dense toward the top of the reaction zone, due to pressure drop and particle size differentiation. Pressure differential between two vertically spaced points in the reactor column can be measured to obtain the average bed density at such portion of the reaction zone. For instance, in a fluidized bed system employing ZSM-5 particles having an apparent packed density of 750 kg/m$^3$ and real density of 2430 kg/m$^3$, an average fluidized bed density of about 300 to 500 kg/m$^3$ is satisfactory.

By virtue of the turbulence experienced in the turbulent regime, gas-solid contact in the catalytic reactor is improved, providing at least 70% ethene conversion, enhanced selectivity and temperature uniformity. One main advantage of this technique is the inherent control of bubble size and characterisitic bubble lifetime. Bubbles of the gaseous reaction mixture are small, random and short-lived, thus resulting in good contact between the gaseous reactants and the solid catalyst particles.

In an alternative embodiment, the process comprises contacting a $C_1$-$C_4$ aliphatic oxygenate feedstock in a primary fluidized bed reaction zone of a riser reaction system with a shape selective medium pore crystalline metallosilicate catalyst under oxygenate conversion conditions to obtain a primary effluent comprising ethylene and $C_3$+ olefins; withdrawing the primary effluent; separating the primary effluent into a gaseous stream rich in ethylene and a liquid stream comprising $C_3$+ olefins; contacting the liquid stream comprising $C_3$+ olefins with a shape selective medium pore crystalline metallosilicate catalyst in a fixed bed reaction zone at elevated temperature and pressure to obtain a product stream comprising hydrocarbons boiling in the gasoline and distillate range; contacting the ethylene-rich stream with a shape selective medium pore crystalline metallosilicate catalyst in a secondary fluidized bed reaction zone of the riser reaction system under oligomerization conditions to obtain a secondary effluent comprising unreacted ethylene and heavier hydrocarbons; withdrawing the secondary effluent; and combining the secondary effluent with the $C_1$-$C_4$ aliphatic oxygenate feedstock for further conversion in the primary fluidized bed reaction zone.

The above-described riser reaction system allows for a mixed feed to the oxygenates conversion reaction zone. The effluent from the oligomerization reaction zone comprises $C_3$+ olefins, $C_6$+ aromatics and unreacted ethene which function as reactive components in the aliphatic oxygenates conversion reactor.

The present invention provides a process for integrating catalyst flow in a multi-stage system. The process comprises maintaining a primary fluidized bed reactor stage at oxygenate conversion conditions, the reactor containing solid catalyst particles comprising medium pore shape selective crystalline aluminosilicate; maintaining a secondary fluidized bed reactor stage at olefins oligomerization conditions, the reactor containing solid catalyst particles comprising medium pore shape selective crystalline aluminosilicate; withdrawing from the secondary fluidized bed reactor stage at least a portion of partially deactivated solid catalyst particles; and adding the partially deactivated solid catalyst particles to the primary fluidized bed reactor stage.

Preferably, the solid catalyst particles in the secondary fluidized bed reactor stage have an average steady state alpha value of about 2 to 20 and the solid catalyst particles in the primary fluidized bed reactor stage have an average steady state alpha value of about 1 to 10.

In situations where the two fluidized bed reactors are operating at pressures which are relatively close to each other, the solid catalyst particles in both reactor stages are preferably passed to a common regenerator and catalyst stripper. Regenerated catalyst particles are then withdrawn from the common regenerator and passed to both the primary and secondary fluidized bed reactor stages.

The feature of a common regenerator for catalyst particles in both reactor stages is conveniently incorporated into the present process. In its simplest form, the process comprises preparing a feedstock for a fixed bed olefins conversion to gasoline and distillate reactor comprising maintaining a reaction system comprising a lower section operatively connected to an upper section, the lower section comprising a secondary fluidized bed containing catalyst particles comprising shape selective medium pore crystalline metallosiliate catalyst and the upper section comprising a primary fluidized bed containing catalyst particles comprising shape selective medium pore crystalline metallosilicate catalyst; contacting a vapor stream comprising ethene with fluidized catalyst particles in the lower section to obtain an effluent comprising unreacted ethene and heavier hydrocarbons; withdrawing the effluent from the lower section; adding a stream comprising a $C_1$-$C_4$ oxygenate or mixtures thereof to the uperr section; adding the lower section effluent with fluidized catalyst particles to the upper section to produce oligomerizable $C_3$+ olefins.

The lower section effluent containing fluidized catalyst particles can be added to the upper section of the reaction system either above the apex of the primary fluidized bed or directly into the primary fluidized bed. If further conversion is desired then the lower section effluent is contacted with catalyst in the primary fluidized bed. Otherwise the lower section effluent can be added above the apex of said fluidized bed so as to avoid further conversion. In both cases catalyst fines entrained in lower section effluent will be captured by cyclones in the oxygenates conversion reactor.

The process further comprises withdrawing the feedstock comprising $C_3+$ olefins from the riser reaction system; and adding the feedstock to a fixed bed reactor system maintained under conditions for the conversion of lower molecular weight $C_3+$ olefins to hydrocarbons boiling in the gasoline and/or distillate range and containing catalyst particles comprising shape selective medium pore crystalline metallosilicate catalyst. From the fixed bed reactor system there is withdrawn a product comprising hydrocarbons boiling in the gasoline and/or distillate range.

Catalyst inventory in the lower section of the reaction system is integrated with catalyst inventory in the upper section of the system by a process comprising withdrawing at least a portion of the catalyst particles in admixture with the effluent from the lower section; adding the withdrawn catalyst particles without separation from effluent to the upper section; withdrawing at least a portion of catalyst particles from the upper section; adding the particles withdrawn from the upper section to a catalyst regeneration system; regenerating the catalyst particles to obtain a reactivated catalyst; and returning reactivated catalyst to the lower section. The reactivated catalyst is lifted into the reaction system by the action of an ethene-rich feedstream which is forced upwardly through the lower section of the riser reaction system. A portion of the oxygenate feedstream can be combined with the ethene-rich feedstream to function as a lift gas for the reactivated catalyst.

In a preferred embodiment, the crystalline metallosilicate catalyst particles in both the secondary fluidized bed of the lower section and the primary fluidized bed of the upper section comprise an aluminosilicate zeolite having the structure of ZSM-5. Most preferably, the zeolite comprises ZSM-5.

The continuous multi-stage process comprises contacting the ethylene-rich stream in a high severity riser reactor at elevated temperature and pressure with a zeolite oligomerization catalyst having an average alpha value of at least about 2 to provide a hydrocarbon effluent comprising heavier hydrocarbons and unreacted light olefin; combining the hydrocarbon effluent with a stream comprising $C_1-C_4$ aliphatic oxygenates to obtain a feedstock for an oxygenate conversion reactor; and contacting the combined feedstock in a fluidized bed oxygenate conversion reactor with a zeolite oxygenate conversion catalyst to obtain a product comprising $C_3+$ oligomerizable olefins. The $C_3+$ oligomerizable olefins are contacted with a medium pore shape selective crystalline aluminosilicate catalyst under conversion conditions to obtain a product comprising hydrocarbons boiling in the gasoline and/or distillate range, which are then withdrawn as product.

In a preferred embodiment, the high severity riser reactor is operated at substantially the same pressure as the fluidized bed oxygenate conversion reactor. This allows for the use of a common regenerator, spent catalyst stripper and fines recovery section for the MOG and MTO processes. A typical MTO operation is conducted over a bed of HZSM-5 catalyst at about 340 kPa (50 psia) at 515 degrees C. (960 degrees F.) at a space velocity (WHSV) of 0.5-1 to convert about 50% of the oxygenated organic feedstock components to hydrocarbons. Table I lists the organic hydrocarbon product distribution from a typical MTO process.

TABLE I

| MTO PRODUCT DISTRIBUTION | |
|---|---|
| Component | wt. % |
| Methane | 2.26 |
| Ethylene | 8.65 |
| Ethane | .59 |
| Propylene | 22.68 |
| Propane | 4.09 |
| $C_4$ hydrocarbons | 22.54 |
| $C_5$ hydrocarbons | 12.42 |
| $C_6$ hydrocarbons | 7.36 |
| $C_7$ hydrocarbons | 5.99 |
| $C_8+$ hydrocarbons | 13.41 |
| Unknown HC as $C_5$ | .01 |

Applicants have discovered a continuous multistage fluidized bed catalytic process for converting a $C_1-C_4$ aliphatic oxygenate feedstock to liquid hydrocarbon products comprising: maintaining a primary fluidized bed of finely divided acid medium pore zeolite catalyst particles in steady state equilibrium fluidized condition under oxygenate conversion reaction conditions, wherein the average catalyst particle acid value is maintained at a first predetermined value to optimize conversion of oxygenate feedstock to lower olefins comprising ethylene and $C_3+$ olefins; contacting a $C_1-C_4$ aliphatic oxygenate feedstock with acid zeolite catalyst particles in the primary fluidized bed to produce a lower olefin effluent; withdrawing the lower olefin effluent and separating the effluent to obtain a first effluent fraction rich in ethylene and a second effluent fraction rich in $C_3+$ olefins; maintaining a secondary fluidized bed of finely divided acid medium pore zeolite catalyst particles in steady state equilibrium fluidized condition under reaction severity conditions sufficient to convert a major amount of ethylene, wherein the average catalyst particle acid value is maintained at a second predetermined acid value higher than said first value by addition of fresh acid medium pore zeolite catalyst particles to optimize conversion of ethylene to $C_5+$ hydrocarbons; contacting the first effluent fraction rich in ethylene with acid zeolite catalyst particles in the secondary fluidized bed to obtain a $C_5+$ hydrocarbon effluent; withdrawing acid catalyst particles from the secondary fluidized bed; adding a first portion of withdrawn secondary fluidized bed particles to the primary fluidized bed; adding a second portion of withdrawn secondary fluidized bed particles to a catalyst regeneration zone; withdrawing deactivated acid catalyst particles from the primary fluidized bed to maintain equilibrium conditions therein; adding withdrawn primary fluidized bed particles to the catalyst regeneration zone; oxidatively regenerating catalyst particles from said primary and secondary fluidized beds in the catalyst regeneration zone; withdrawing regenerated catalyst from the oxidative regeneration zone; and adding regenerated catalyst to at least the secondary fluidized bed.

An apparatus useful for increasing the yield of liquid hydrocarbons from a $C_1-C_4$ aliphatic oxygenate feedstock is disclosed. The apparatus comprises a primary fluidized bed reaction zone containing shape selective medium pore crystalline metallosilicate catalyst; a primary separation zone for separating a primary effluent into a gaseous stream rich in ethylene and a liquid stream comprising $C_3+$ olefins; a means for passing said primary effluent from primary reaction zone to primary separation zone; a fixed bed reaction zone containing shape selective medium pore crystalline metallosilicate catalyst; a means for passing the liquid stream from the primary separation zone to the fixed bed reaction zone; a secondary fluidized bed reaction zone containing shape selective medium pore crystalline metallosilicate catalyst; a means for passing the gaseous stream from the primary separation zone to the secondary reaction zone; a secondary separation zone for separating a secondary effluent into a gaseous stream comprising ethylene and a liquid stream comprising heavier hydrocarbons; a means for passing said secondary effluent from secondary reaction zone to secondary separation zone; a means for passing at least a portion of liquid stream from the secondary separation zone to the fixed bed reaction zone; a means for withdrawing from the fixed bed reaction zone a product stream comprising hydrocarbons boiling in the gasoline and distillate range; a common catalyst regeneration zone for oxidative regeneration of deactivated catalyst from both primary and secondary reaction zone; a means for passing deactivated catalyst from primary reaction zone to catalyst regeneration zone; a means for passing a first portion of deactivated catalyst from secondary reaction zone to said primary reaction zone; a means for passing a second portion of deactivated catalyst from secondary reaction zone to said catalyst regeneration zone; and a means for passing reactivated catalyst from common catalyst regeneration zone to both the primary and secondary fluidized bed reaction zones.

An apparatus is disclosed for converting a $C_1$–$C_4$ aliphatic oxygenate feedstock to hydrocarbon products. The apparatus comprises a lower section comprising a secondary fluidized bed containing shape selective crystalline zeolite catalyst particles having an apparent average steady state alpha value of about 2 to 20; an operatively connected upper section comprising a primary fluidized bed containing shape selective crystalline zeolite catalyst particles having an apparent average steady state alpha value of about 1 to 10; a means for adding an ethene-containing feedstream to the lower section; a means for passing a secondary effluent containing $C_3+$ olefins, unreacted ethene and catalyst particles from the lower section to the upper section, said means either adding the secondary effluent directly to the primary fluidized bed for contact with zeolite catalyst or adding the secondary effluent above the uppermost level of the primary fluidized bed for admixture with a primary effluent; a means for adding a feedstream comprising a $C_1$ to $C_4$ oxygenate or mixtures thereof to the primary fluidized bed of the upper section; a means for withdrawing a primary effluent from the upper section; a common catalyst regeneration zone for oxidative regeneration of deactivated catalyst from both the primary and secondary fluidized beds; a means for passing deactivated catalyst from upper level to catalyst regeneration zone; a means for passing reactivated catalyst from the regeneration zone to the ethene-containing feedstream means; and a means for adding fresh catalyst to the ethene-containing feedstream means.

Alternatively, the apparatus further comprises a means for passing a portion of said oxygenate feedstream to the ethene-containing feedstream means.

Figure 1:
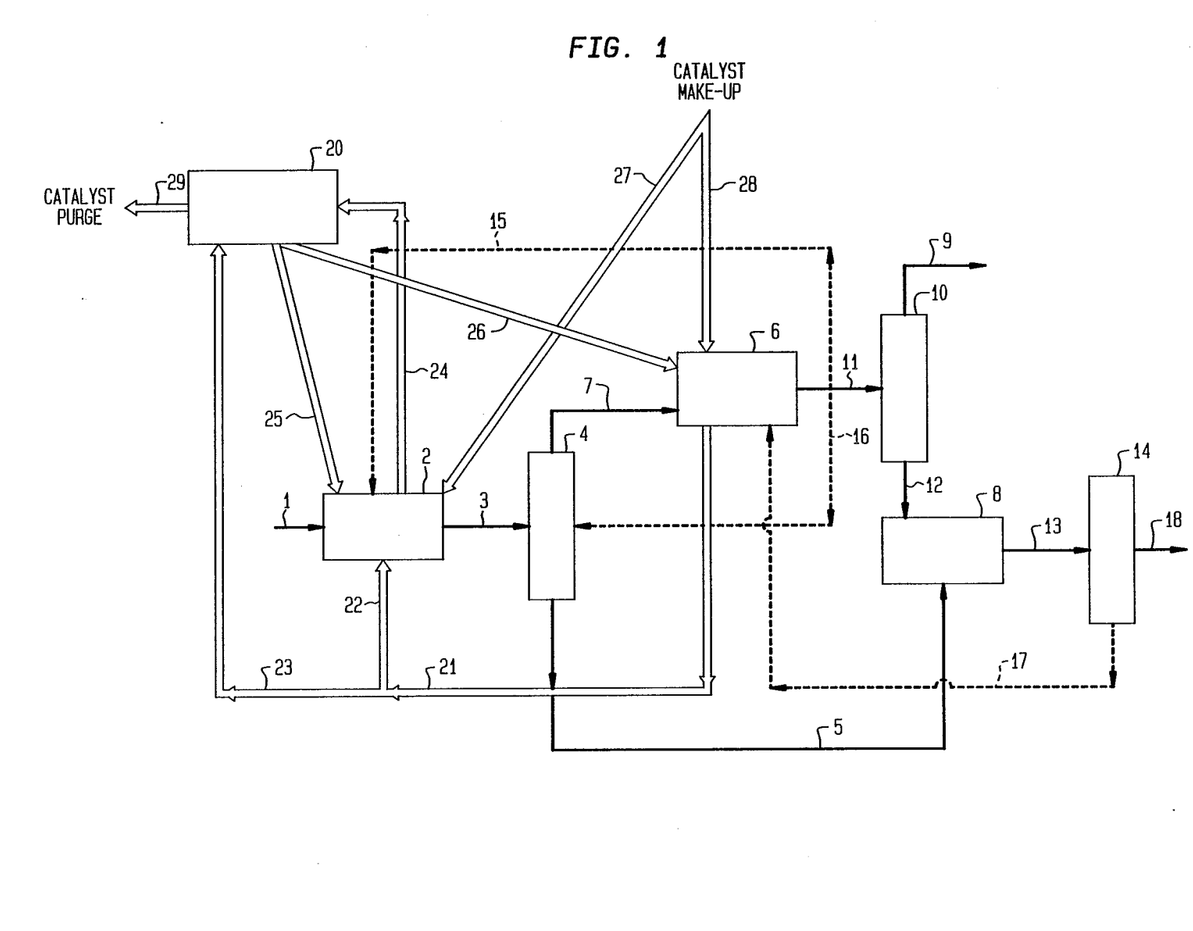
FIG. 1 is a process flow sheet showing the major unit operations, process streams, and catalyst handling streams.

Referring to FIG. 1, a $C_1$–$C_4$ oxygenate feedstock, preferably a mixture of methanol and dimethyl ether, is passed as by line 1 to a primary fluidized bed oxygenates conversion reactor 2 containing a shape selective medium pore crystalline metallosilicate catalyst. The reactor is maintained at a conversion temperature of about 450 degrees C. to 532 degrees C. and a pressure of about 69 KPa to 900 KPa. The amount of oxygenate converted per pass is about 100%.

The crystalline metallosilicate catalyst has an average alpha value of about 1 to 10. The catalyst preferably comprises an aluminosilicate zeolite having the structure of ZSM-5. In a most preferred embodiment, the catalyst comprises ZSM-5.

An effluent comprising unreacted oxygenate, ethene, $C_3+$ olefins, ethane, and other light gases is withdrawn from the oxygenates conversion reactor as by line 3. The entire effluent is conducted via line 3 to a separation unit 4 wherein a vapor stream containing a major amount of ethene exits overhead via line 7, and a liquid hydrocarbon stream comprising $C_3+$ olefins such as propene, n-butene, isobutene, the isomeric pentenes, and hexene isomers is withdrawn via line 5.

The ethene-rich stream, which contains a significant quantity of unrecoverable $C_3+$ olefins which are also upgraded to gasoline range hydrocarbons, enters a secondary fluidized bed reaction zone 6 maintained under olefins oligomerization conditions to upgrade the ethene to a $C_5$–$C_{10}$ hydrocarbon product boiling in the gasoline range. The fluidized bed contains catalyst comprising shape selective medium pore crystalline metallosilicate particles. In a preferred embodiment the catalyst particles are aluminosilicate materials such as zeolites. Most preferably the catalyst is a zeolite having the structure of ZSM-5 with an average alpha value of about 2 to 50.

The fluidized bed reaction zone 6 is maintained at an olefins oligomerization temperature of about 232 degrees C. to 532 degrees C. and a pressure of about 69 KPa to 2,061 KPa. The amount of ethene converted per pass is more than about 70%, preferably about 93 to 96%.

A reaction effluent comprising unreacted ethene, $C_5$–$C_{10}$ hydrocarbons boiling in the gasoline range, and light gases is withdrawn from fluidized bed reaction zone 6 and passed as by line 11 to a separation column 10. An overhead containing unreacted ethene is withdrawn from the separator and sent to fuel main via line 9. A bottoms stream comprising $C_5$–$C_{10}$ hydrocarbons boiling in the gasoline range is withdrawn from the separation column 10 and passed via line 12 to a fixed bed reaction zone 8. The bottoms stream is optionally passed directly to the gasoline pool.

A second feed to fixed bed reaction zone 8 is the bottoms stream obtained from separation unit 4. The bottoms stream comprising $C_3+$ olefins enters the fixed bed reactor 8 as by line 5.

The fixed bed reaction zone 8 contains a shape selective medium pore crystalline metallosilicate catalyst which has an average alpha value of about 3 to 80. The catalyst preferably comprises an aluminosilicate zeolite having the structure of ZSM-5. In a most preferred embodiment, the catalyst comprises ZSM-5.

The fixed bed reactor is maintained at a temperature of about 204 degrees C. to 315 degrees C. and a pressure of about 2,747 KPa to 20,604 KPa. A higher pressure is employed to obtain lube components in the reaction product.

When $C_3+$ olefins contact the metallosilicate catalyst contained in the fixed bed reactor, they are oligomerized to produce hydrocarbons boiling in the gasoline and/or distillate range. A crude product stream comprising gasoline and/or distillate hydrocarbons is withdrawn from the fixed bed reactor via line 13. The product stream can be purified in a series of separation steps or sent to a reaction zone for further processing. In a preferred embodiment, ethene-containing light components from the fixed bed reaction zone are separated in fractionation column 14 and returned as by line 17 to zone 6 in order to maximize $C_5+$ hydrocarbon yield. The light components optionally contain $C_3$–$C_4$ hydrocarbons. Hydrocarbon product containing $C_5+$ hydrocarbons, including gasoline and optionally distillate and lube components, is withdrawn as by line 18.

In an alternative embodiment, the reaction effluent withdrawn from fluidized bed reaction zone 6 via line 11 is passed as by line 15 to the fluidized bed oxygenates conversion zone 2. The effluent from reaction zone 6 can be admixed with oxygenates feedstock prior to entering fluidized bed 2. Alternatively, at least a portion of reaction effluent withdrawn from secondary zone 6 as by line 11 can be returned to separation unit 4 via line 16.

With regard to catalyst flow, partially deactivated catalyst particles are withdrawn from secondary fluidized bed 6 as by line 21. A first portion of said catalyst particles is added to the primary fluidized bed via line 22 to preserve equilibrium conditions in the oxygenates conversion reactor. A second portion of said withdrawn catalyst particles is optionally added to catalyst regeneration unit 20 via line 23 where catalyst is regenerated as by oxidative means. The regeneration unit 20 also serves to reactivate catalyst particles which are withdrawn from primary fluidized bed 2 via line 24.

From the common catalyst regenerator 20 is withdrawn reactivated catalyst particles which are added to either one or both fluidized beds. Catalyst particles can be added to the primary fluidized bed as by line 25 and to the secondary fluidized bed via line 26. In a preferred embodiment, regenerated catalyst is added to the secondary fluidized bed 6 along with catalyst make-up, which is added as by line 28. Catalyst make-up can be added to primary fluidized bed 2 via line 27. Catalyst purge is withdrawn from regenerator 20 via line 29.

Figure 2:
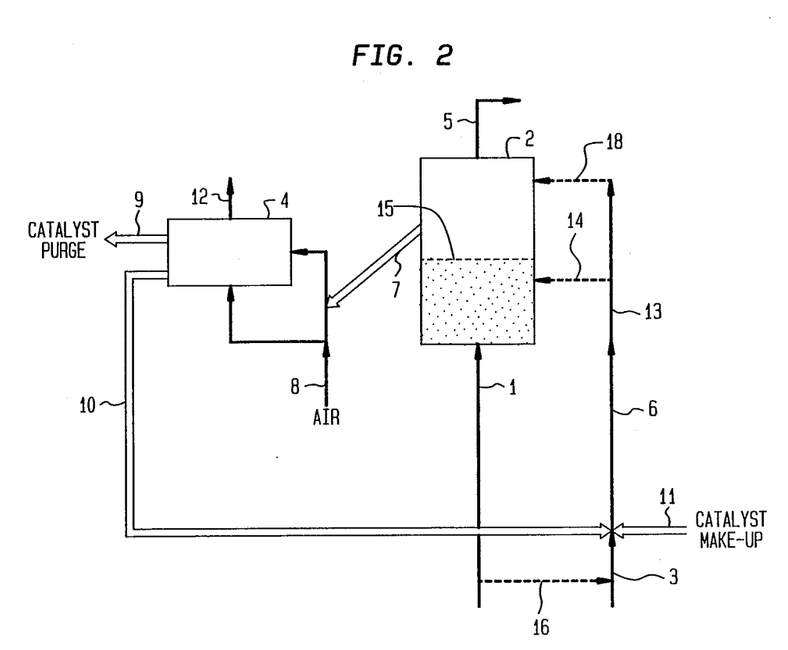
FIG. 2 is a process flow diagram for an alternative system incorporating a series of fluidized bed catalytic conversion reactors in a riser reaction system.

FIG. 2 shows a reacton system comprising a fluidized bed olefins upgrading riser reactor 6 and an operatively connected fluidized bed oxygenates conversion reactor 2. The reaction system permits successful upgrading of an ethene-rich stream which is a byproduct from conversion of $C_1$–$C_4$ oxygenates to olefins. In another embodiment an ethene-rich stream obtained from any refinery source is employed as a feed to the riser reactor.

Referring to FIG. 2, a $C_1$–$C_4$ oxygenate feedstock, preferably an equilibrium mixture of methanol and dimethylether, is passed via line 1 to fluidized bed in reaction zone 2 where it contacts finely divided solid catalyst particles comprising a shape selective medium pore crystalline metallosilicate. The metallosilicate preferably comprises an aluminosilicate zeolite having the structure of ZSM-5. Most preferably, the catalyst comprises ZSM-5.

A product comprising $C_3+$ oligomerizable olefins is withdrawn from reactor 2 and passed to a separation unit (not shown). From separation unit is withdrawn an overhead stream comprising ethene and a bottoms stream containing $C_3+$ olefins.

The bottoms stream rich in $C_3+$ olefins is an excellent feedstock for a catalytic reaction system maintained under conditions for oligomerizing olefins to gasoline, distillate and lube range hydrocarbons. The $C_3+$ olefins-rich bottoms stream can be passed directly to the catalytic reaction system or mixed with other olefinic feedstock prior to entering the system.

The reaction system for producing gasoline, distillate and lube range hydrocarbons contains a shape selective medium pore crystalline metallosilicate catalyst having an average steady state alpha value of about 3 to 80. The catalyst preferably comprises an aluminosilicate zeolite having the structure of ZSM-5. In a most preferred embodiment, the catalyst comprises ZSM-5. From the reaction system is withdrawn a product comprising hydrocarbons boiling in the gasoline and/or distillate range.

An ethene-containing overhead stream from the separation unit (not shown) enters secondary stage fluidized bed riser reactor 6 as by line 3. In an alternative embodiment, a portion of oxygenate feed is added to the ethene-containing stream as by line 16. Ethene contacts solid catalyst particles comprising a crystalline shape selective medium pore metallosilicate, preferably ZSM-5 zeolite, under high severity reaction conditions. The catalyst has an average steady state alpha value of about 2 to 20. At least a portion of the ethene is catalytically converted to $C_5$–$C_{10}$ hydrocarbons boiling in the gasoline range.

An effluent comprising $C_5$–$C_{10}$ hydrocarbons and unreacted ethene is withdrawn from riser reactor 6 as by line 13 and admixed with the reactor effluent via line 18 or the reactor bed via line 14 in primary stage reaction zone 2. Oxygenate enters reactor 2 via line 1. The apex or uppermost level of fluidized bed in reactor 2 is shown by segmented line 15.

The light hydrocarbon stream recovered from the oxygenates conversion stage via line 5 preferably contains a major amount of $C_2$–$C_4$ olefins. The novel system includes a separation unit for recovering ethene from the primary stage olefinic vapor effluent including a sorption tower operatively connected to selectively sorb $C_3+$ hydrocarbons from the olefinic vapor effluent in a liquid sorption stream. Since the separation unit is usually operated at a pressure higher than the primary stage and lower than the secondary conversion stage, vapor compression means for the primary stage light hydrocarbon stream and means for pressurizing and heating the liquid sorption stream containing $C_3+$ sorbate are provided.

A suitable sorption fractionation system is described in U.S. patent application Ser. No. 508,779, filed June 29, 1983 (Hsia et al), now U.S. Pat. No. 4,479,812 the disclosure of which is incorporated herein by reference. The $C_2$- and $C_3+$ separation is accomplished by a single absorber-stripper using gasoline recycle as absorbent and pumparounds for removing absorption heat. The amount of absorbent is set by the amount of recycle gasoline required in the $C_3$- olefins conversion reaction thereby allowing the tower bottom stream to be pumped directly to the reactor pressure. Without using refrigeration, this tower efficiently and effectively separates the ethylene and light gases ($H_2$, $C_2H_6$ and $CH_4$) from the $C_3+$ hydrocarbon.

The gasoline sorbent is an aliphatic hydrocarbon mixture boiling in the normal gasoline range of about 50 to 165 C. (125 to 330 F.), with minor amounts of $C_4$–$C_5$ alkanes and alkenes. The process may be operated with a mole ratio of about 0.2 moles to about 10 moles of gasoline per mole of $C_3+$ hydrocarbons in the feedstock, with optimum operation utilizing a sorbent:sorbate molar ratio about 1:1 to 1.5:1.

In the process design of FIG. 2 catalyst flow is upward through riser reactor 6 and is passed to the turbulent regime fluidized bed reactor 2. Partially deactivated catalyst, including both oligomerization catalyst and oxygenates conversion catalyst, is withdrawn as by line 7, lifted by air as by line 8, and contacted with an oxygen-containing gas in a common catalyst regeneration zone 4 for oxidative regeneration. Regenerated catalyst is returned to riser reactor 6 via line 10, and catalyst make-up is added to reactor 6 via line 11. The daily catalyst make-up is about 0.3 wt. % of the total catalyst inventory. A catalyst purge is withdrawn from regeneration unit 4 via line 9. Flue gas is withdrawn from regenerator 4 as by line 12.

An additional feature of the present design as shown in FIG. 2 is a combined catalyst fines filtration system and process wherein the catalyst fines from both the primary turbulent regime fluidized bed oxygenates conversion reactor and the secondary olefins oligomerization riser reactor are filtered and recovered in a common system. The system comprises cyclones and/or a sintered metal filter system to recover fines from the combined reactors effluent stream.

It is understood that the various process conditions are given for a continuous system operating at steady state, and that substantial variations in the process are possible within the inventive concept.

In the process for catalytic conversion of olefins to heavier hydrocarbons by catalytic oligomerization using an acid crystalline zeolite, such as a catalyst having the structure of ZSM-5, process conditions can be varied to favor the formation of either gasoline or distillate range products. At moderate temperature and relatively high pressure, the conversion conditions favor distillate range product having a normal boiling point of at least 165° C. (330° F.). Lower olefinic feedstocks containing $C_2$–$C_6$ alkenes may be converted selectively; however, the distillate mode conditions do not convert a major fraction of ethylene. While propene, butene-1 and others may be converted to the extent of 80 to 99% in the distillate mode, only about 10 to 50% of the ethylene component will be consumed. Also, high-pressure pressure conversion of ethene is unfavorable because of the prohibitively high cost of compressing ethene-rich feedstocks. Accordingly, the ethene is advantageously recovered prior to the oligomerization stage. In a preferred embodiment the olefinic feedstock is obtained form lower aliphatic oxygenates, such as methanol or dimethylether (DME). A typical crude methanol feedstock may contain 4 to 17% water, with minor amounts of carbon oxides, methane, DME, etc.

The feedstock is methanol (MeOH), which may be partially dehydrated in a separate process step over gamma-alumina catalyst to yield dimethyl ether (DME) and water. A preliminary dewatering step can be used to provide a feedstock consisting essentially of MeOH and/or DME. The oxygenate is fed continuously under low pressure where it is raised to process temperature, and introduced to the MTO reactor system. The initial dehydration reactor is followed by a catalytic reactor containing zeolite conversion catalyst. The effluent is cooled to condense water and a major amount of $C_5$- liquid hydrocarbons. These liquids are separated from the hydrocarbon vapor in a phase separator. Byproduct water may be recovered from unreacted feedstock and discarded. The liquid hydrocarbon phase and the ethene-rich light hydrocarbon vapor streams are recovered from a separator. A suitable fluid catalyst apparatus is disclosed in U.S. Pat. No. 4,379,123 (Daviduk and Haddad).

While the invention has been described by specific examples and embodiments, there is no intent to limit the inventive concept except as set forth in the following claims.

We claim:

1. A continuous multi-stage process for increasing the yield of liquid hydrocarbons from a $C_1$–$C_4$ aliphatic oxygenate feedstock comprising:
   (a) contacting the feedstock in a primary fluidized bed reaction zone with a shape selective medium pore crystalline metallosilicate catalyst under oxygenate conversion conditions to obtain a primary effluent comprising ethylene and $C_3$ olefins;
   (b) withdrawing the primary effluent;
   (c) separating the primary effluent into a gaseous stream rich in ethylene and a liquid stream comprising $C_3+$ olefins;
   (d) contacting the liquid stream comprising $C_3+$ olefins with a shape selective medium pore crystalline metallosilicate catalyst in a fixed bed reaction zone at elevated temperature and pressure to obtain a product stream comprising hydrocarbons boiling in the gasoline and distillate range;
   (e) contacting the ethylene-rich stream with a shape selective medium pore crystalline metallosilicate catalyst in a secondary fluidized bed reaction zone under oligomerization conditions to obtain a secondary effluent comprising unreacted ethylene and heavier hydrocarbons;
   (f) withdrawing the secondary effluent;
   (g) separating the secondary effluent into a gaseous stream comprising ethylene and a liquid stream comprising heavier hydrocarbons; and
   (h) adding at least a portion of the liquid stream comprising heavier hydrocarbons to the fixed bed reaction zone of step (d), whereby the yield of hydrocarbons boiling in the gasoline and distillate range is increased.

2. The process according to claim 1 wherein the catalyst in step (a) comprises an aluminosilicate zeolite having a silica:alumina molar ratio of at least about 12 and a constraint index of about 1 to 12.

3. The process according to claim 2 wherein the zeolite catalyst comprises HZSM-5 having an average steady state alpha value of about 1 to 10.

4. A process according to claim 1 further comprising:
   (i) withdrawing from the fixed bed reaction zone the product stream;
   (j) separating ethene-containing light components from hydrocarbons boiling in the gasoline and distillate range; and
   (k) adding the light components to the secondary fluidized bed reaction zone.

5. The process according to claim 1 wherein the catalyst in step (e) comprises an aluminosilicate zeolite having a silica:alumina molar ratio of at least about 12 and a constraint index of about 1 to 12.

6. The process according to claim 5 wherein the zeolite catalyst comprises HZSM-5 having an average steady state alpha value of about 2 to 20, and the reaction severity index (R.I.) is maintained at about 0.1:1 to 1:1 in the secondary fluidized zone.

7. The process according to claim 1 wherein the $C_1$-$C_4$ aliphatic oxygenate feedstock comprises methanol, dimethyl ether, or mixtures thereof.

8. A process for increasing the yield of liquid hydrocarbons from a $C_1$-$C_4$ aliphatic oxygenate feestock comprising:
    contacting the feedstock under oxygenate conversion conditions in a primary fluidized bed reaction system with a crystalline medium pore shape selective zeolite catalyst;
    withdrawing an effluent comprising ethene and $C_3$+ olefins;
    separating the effluent into a primary bottoms stream comprising $C_3$+ olefins and a primary overhead stream comprising ethene; and
    contacting the primary overhead stream comprising ethene under high severity oligomerization conditions in a secondary fluidized bed reaction system with a crystalline medium pore shape selective zeolite catalyst.

9. A process according to claim 8 further comprising:
    withdrawing from the secondary fluidized bed reaction system a product comprising unreacted ethene and $C_3$+ olefins; and
    adding at least a portion of withdrawn product to the primary fluidized bed reaction system.

10. A process according to claim 8 wherein the primary fluidized bed reaction system is maintained at a temperature of about 450 degrees C. to 532 degrees C. and a pressure of about 69 KPa to 900 KPa.

11. A process according to claim 8 wherein the $C_1$-$C_4$ aliphatic oxygenate feedstock comprises dimethyl ether, methanol, or mixtures thereof.

12. A process according to claim 8 wherein the zeolite catalyst in the primary fluidized bed reaction system comprises a catalyst having the structure of ZSM-5.

13. A process according to claim 12 wherein the zeolite catalyst comprises ZSM-5.

14. A process according to claim 8 wherein the zeolite catalyst in the primary fluidized bed reaction system has an average steady state alpha value of about 1 to 10.

15. A process according to claim 8 wherein the zeolite catalyst in the secondary fluidized bed reaction system comprises a catalyst having the structure of ZSM-5.

16. A process according to claim 15 wherein the zeolite catalyst comprises ZSM-5.

17. A process according to claim 8 wherein the zeolite catalyst in the secondary fluidized bed reaction system has an average steady state alpha value of about 2 to 20.

18. A process for integrating catalyst flow in a multistage process comprising:
    maintaining a primary fluidized bed reactor stage at oxygenate conversion conditions, the reactor containing solid catalyst particles comprising medium pore shape selective crystalline siliceous zeolite;
    maintaining a secondary fluidized bed reactor stage at olefins oligomerization conditions, the reactor containing solid catalyst particles comprising medium pore shape selective crystalline aluminosilicate, said reactor being operatively connected to the primary reactor stage;
    withdrawing from the secondary fluidized bed reactor stage at least a portion of partially deactivated solid catalyst particles; and
    adding the partially deactivated solid catalyst particles to the primary fluidized bed reactor stage.

19. A process according to claim 18 wherein the solid catalyst particles in the secondary fluidized bed reactor stage have an average steady state alpha value of about 2 to 20.

20. A process according to claim 18 wherein the solid catalyst particles in the primary fluidized bed reactor stage have an average steady state alpha value of about 1 to 10.

21. A process according to claim 18 further comprising:
    withdrawing solid catalyst particles from primary stage; and
    adding particles to a common catalyst stripper and regenerator.

22. A process according to claim 18 wherein the catalyst particles in both the primary and secondary fluidized bed reactor stages comprise a zeolite having the structure of ZSM-5.

23. A process for preparing a feedstock for a fixed bed olefins conversion to gasoline and distillate reactor comprising:
    maintaining a reaction system comprising a lower section operatively connected to an upper section, the lower section comprising a secondary fluidized bed containing catalyst particles comprising shape selective medium pore crystalline metallosilicate catalyst and the upper section comprising a primary fluidized bed containing catalyst particles comprising shape selective medium pore crystalline metallosilicate catalyst;
    contacting a vapor stream comprising ethene with fluidized catalyst particles in the lower section to obtain an effluent comprising unreacted ethene and heavier hydrocarbons;
    withdrawing the effluent from the lower section;
    adding a stream comprising a $C_1$-$C_4$ oxygenate or mixtures thereof to the upper section; and
    adding the lower section effluent with fluidized catalyst particles to the upper section to produce oligomerizable $C_3$+ olefins 24. A process according to claim 23 further comprising:
    withdrawing the feedstock comprising $C_3$+ *olefins from the reaction system; and*
    adding the feedstock to a fixed bed reactor system maintained under conditions for the conversion of lower molecular weight $C_3$+ olefins to hydrocarbons boiling in the gasoline and/or distillate range and containing catalyst particles comprising shape selective medium pore crystalline metallosilicate catalyst.

25. A process according to claim 24 further comprising integrating the catalyst inventory of the lower section and the upper section of the reaction system comprising:
    withdrawing at least a portion of the catalyst particles in admixture with the effluent from the lower section;
    adding the withdrawn catalyst particles without separation from effluent to the upper section;
    withdrawing at least a portion of catalyst particles from the upper section;

adding the particles withdrawn from the upper section to a catalyst regeneration system;

regenerating the catalyst particles to obtain a reactivated catalyst; and returning reactivated catalyst to the lower section.

26. A process according to claim 23 wherein the crystalline metallosilicate catalyst particles in both the secondary fluidized bed of the lower section and the primary fluidized bed of the upper section comprise an aluminosilicate zeolite having the structure of ZSM-5.

27. A process according to claim 26 wherein the aluminosilicate zeolite comprises ZSM-5.

28. A process according to claim 23 wherein the crystalline metallosilicate particles in the secondary fluidized bed of the lower section have an average steady state alpha value of about 2 to 20.

29. A process according to claim 23 wherein the crystalline metallosilicate particles in the primary fluidized bed of the upper section have an average steady state alpha value of about 1 to 20.

30. A process according to claim 23 wherein the $C_1$–$C_4$ oxygenate comprises methanol, dimethyl ether, or mixtures thereof.

31. A continuous multi-stage process for upgrading a hydrocarbon stream rich in ethylene comprising:

contacting the ethylene-rich stream in a high severity riser reactor at elevated temperature and pressure with a zeolite oligomerization catalyst having an average steady state alpha value of at least about 2 to provide a hydrocarbon effluent comprising heavier hydrocarbons and unreacted light olefin;

adding the hydrocarbon effluent and a stream comprising $C_1$–$C_4$ aliphatic oxygenates to an oxygenate conversion reactor containing zeolite oxygenate conversion catalyst to obtain a product comprising $C_3+$ oligomerizable olefins.

32. The process according to claim 31 further comprising: withdrawing the $C_3+$ oligomerizable olefins and contacting with a medium pore shape selective crystalline aluminosilicate catalyst under conversion conditions to obtain a product comprising hydrocarbons boiling in the gasoline and/or distillate range.

33. The process according to claim 31 wherein the high severity riser reactor is operated at substantially the same pressure as the fluidized bed oxygenate conversion reactor.

34. The process according to claim 31 wherein both the oligomerization catalyst and the oxygenate conversion catalyst are withdrawn upon partial deactivation and contacted with an oxygen-containing gas in a common catalyst regeneration zone for oxidative regeneration.

35. The process according to claim 34 wherein regenerated catalyst is withdrawn from the regeneration zone and lifted through the high severity riser reactor by the action of the ethylene-rich stream.

36. The process according to claim 31 wherein the zeolite oxygenate conversion catalyst has an average steady state acid cracking alpha-value of about 1 to 20.

37. The process according to claim 31 wherein the $C_1$–$C_4$ aliphatic oxygenates comprise methanol, dimethyl ether, or mixtures thereof.

38. The process according to claim 31 wherein the zeolite oligomerization catalyst has an average steady state acid cracking alpha-value of about 2 to 20.

39. A continuous multistage fluidized bed catalytic process for converting a $C_1$–$C_4$ aliphatic oxygenate feedstock to liquid hydrocarbon products comprising:

maintaining a primary fluidized bed of finely divided acid medium pore zeolite catalyst particles in steady state equilibrium fluidized condition under oxygenate conversion reaction conditions, wherein the average catalyst particle acid value is maintained at a first predetermined value to optimize conversion of oxygenate feedstock to lower olefins comprising ethylene and $C_3+$ olefins;

contacting a $C_1$–$C_4$ aliphatic oxygenate feedstock with acid zeolite catalyst particles in the primary fluidized bed to produce a lower olefin effluent;

withdrawing the lower olefin effluent and separating the effluent to obtain a first effluent fraction rich in ethylene and a second effluent fraction rich in $C_3+$ olefins;

maintaining a secondary fluidized bed of finely divided acid medium pore zeolite catalyst particles in steady state equilibrium fluidized condition under reaction severity conditions sufficient to convert a major amount of ethylene, wherein the average catalyst particle acid value is maintained at a second predetermined acid value higher than said first value by addition of fresh acid medium pore zeolite catalyst particles to optimize conversion of ethylene to $C_5+$ hydrocarbons;

contacting the first effluent fraction rich in ethylene with acid zeolite catalyst particles in the secondary fluidized bed to obtain a $C_5+$ hydrocarbon effluent;

withdrawing acid catalyst particles from the secondary fluidized bed;

adding a first portion of withdrawn secondary fluidized bed particles to the primary fluidized bed;

adding a second portion of withdrawn secondary fluidized bed particles to a catalyst regeneration zone;

withdrawing deactivated acid catalyst particles from the primary fluidized bed to maintain equilibrium conditions therein;

adding withdrawn primary fluidized bed particles to the catalyst regeneration zone;

oxidatively regenerating catalyst particles from said primary and secondary fluidized beds in the catalyst regeneration zone;

withdrawing regenerated catalyst from the oxidative regeneration zone; and adding regenerated catalyst to at least the secondary fluidized bed.

40. The process of claim 39 wherein the secondary fluidized bed is maintained under reaction conditions of temperature, space velocity, pressure and catalyst acidity to control conversion of ethylene-containing olefinic light gas to heavier hydrocarbons, wherein production of $C_3$ components is maintained at a propane:propene ratio of about 0.1:1 to 1:1.

41. The process of claim 39 wherein said second effluent fraction rich in $C_3+$ olefins is catalytically upgraded to $C_{10}+$ distillate range hydrocarbon product by contacting with an acid medium pore shape selective zeolite under distillate production conditions at high pressure and moderate temperature to convert $C_3+$ olefins.

42. A process according to claim 39 wherein the primary fluidized bed is maintained at a temperature of about 450 degrees C. to 532 degrees C. and a pressure of about 69 KPa to 900 KPa.

43. A process according to claim 39 wherein the secondary fluidized bed is maintained at a temperature of about 232 degrees C. to 532 degrees C. and a pressure of about 69 KPa to 2061 KPa.

44. A process according to claim 39 wherein the amount of ethylene converted in the secondary fluidized bed is greater than about 70%.

45. A process according to claim 44 wherein the amount of ethylene conversion is about 93% to 96%.

46. A process according to claim 39 wherein the acid medium pore zeolite catalyst particles comprise a zeolite having the structure of ZSM-5.

47. A process according to claim 46 wherein the zeolite comprises ZSM-5.

48. A process according to claim 39 wherein the $C_1$–$C_4$ aliphatic oxygenate feedstock comprises methanol, dimethyl ether, or mixtures thereof.

* * * * *